United States Patent
Urso

(10) Patent No.: US 9,510,921 B1
(45) Date of Patent: Dec. 6, 2016

(54) HIGH-SPEED AUTOMATIC DENTAL FLOSSER

(71) Applicant: Charles Louis Urso, Waltham, MA (US)

(72) Inventor: Charles Louis Urso, Waltham, MA (US)

(*) Notice: Subject to any disclaimer, the term of this patent is extended or adjusted under 35 U.S.C. 154(b) by 168 days.

(21) Appl. No.: 14/121,927

(22) Filed: Nov. 4, 2014

(51) Int. Cl.
*A61C 15/04* (2006.01)

(52) U.S. Cl.
CPC ........... *A61C 15/047* (2013.01); *A61C 15/048* (2013.01); *A61C 15/046* (2013.01)

(58) Field of Classification Search
CPC  A61C 15/046; A61C 15/047; A61C 15/048; A61C 15/04; A46B 15/0071; A46B 15/0073
USPC .................................. 132/324, 325
See application file for complete search history.

(56) References Cited

U.S. PATENT DOCUMENTS

| | | | |
|---|---|---|---|
| 301,055 A * | 6/1884 | Greene ................ | A61C 15/046 132/309 |
| 2,450,635 A | 10/1948 | Dembenski | |
| 2,515,509 A | 7/1950 | Green | |
| 3,830,247 A * | 8/1974 | Kaphalakos ......... | A61C 15/043 132/322 |
| 3,902,510 A | 9/1975 | Roth | |
| 4,005,721 A | 2/1977 | Yasumoto | |
| 4,008,728 A * | 2/1977 | Sanchez ............... | A61C 15/046 132/324 |
| 4,338,957 A | 7/1982 | Meibauer | |
| 4,586,521 A | 5/1986 | Urso | |
| 4,706,695 A | 11/1987 | Urso | |
| 4,727,894 A | 3/1988 | Meibauer | |
| 5,062,241 A | 11/1991 | DeLand | |
| 5,184,632 A | 2/1993 | Gross et al. | |
| 5,188,133 A | 2/1993 | Romanus | |
| 5,207,773 A * | 5/1993 | Henderson ........... | A61C 15/047 132/322 |
| 5,224,500 A | 7/1993 | Stella | |
| 5,323,796 A | 6/1994 | Urso | |
| 5,450,866 A * | 9/1995 | Wang ................... | A61C 15/046 132/324 |
| 5,657,780 A | 8/1997 | Giacopuzzi | |
| 5,678,578 A | 10/1997 | Kossak et al. | |
| 5,749,380 A | 5/1998 | Zebuhr | |
| 5,769,102 A | 6/1998 | Zebuhr | |
| 5,816,271 A | 10/1998 | Urso | |
| 5,947,133 A | 9/1999 | Kossak et al. | |
| 6,092,536 A | 7/2000 | Owens | |
| 6,823,875 B2 | 11/2004 | Hotta et al. | |
| 7,392,810 B2 | 7/2008 | Apotheker et al. | |
| 8,291,537 B2 | 10/2012 | Gall et al. | |
| 8,505,557 B1 * | 8/2013 | Urso ..................... | A46B 9/045 132/322 |
| 2002/0106607 A1 | 8/2002 | Horowitz | |
| 2007/0000515 A1 * | 1/2007 | Yang .................... | A61C 15/047 132/322 |
| 2007/0204878 A1 * | 9/2007 | Apotheker ........... | A61C 15/048 132/322 |
| 2008/0257377 A1 * | 10/2008 | Burrows .............. | A61C 15/043 132/322 |
| 2010/0139689 A1 * | 6/2010 | Couch .................. | A61C 15/047 132/322 |

* cited by examiner

FOREIGN PATENT DOCUMENTS

WO   WO 2007/123840   11/2007

*Primary Examiner* — Tatiana Nobrega

(57) ABSTRACT

A high-speed automatic dental flosser (10) includes a detachably connected flossing attachment (12) having a pair of flossing tines (46) and (48) for supporting a movable floss span (47) to floss teeth, a floss supply spool (15) for continuously supplying fresh floss spans, and a floss take-up spool (17) includes a built-in floss gripper. A power driver (14) includes a dual-shaft geared motor (20) having an anterior drive shaft (22) drivingly connectable to the take-up spool and a posterior drive shaft (24) for drivingly rotating an eccentrically supported weight (40) to oscillate the floss span. An electric momentary switch (28) actuates the motor energized by a power cell (26). A built-in floss-cutter (29) is provided for cutting off used floss. An alternative flossing attachment (12B) includes an alternative floss gripper built into a take-up spool (39). Additional flossing attachments (12C) and (12D) are included.

11 Claims, 2 Drawing Sheets

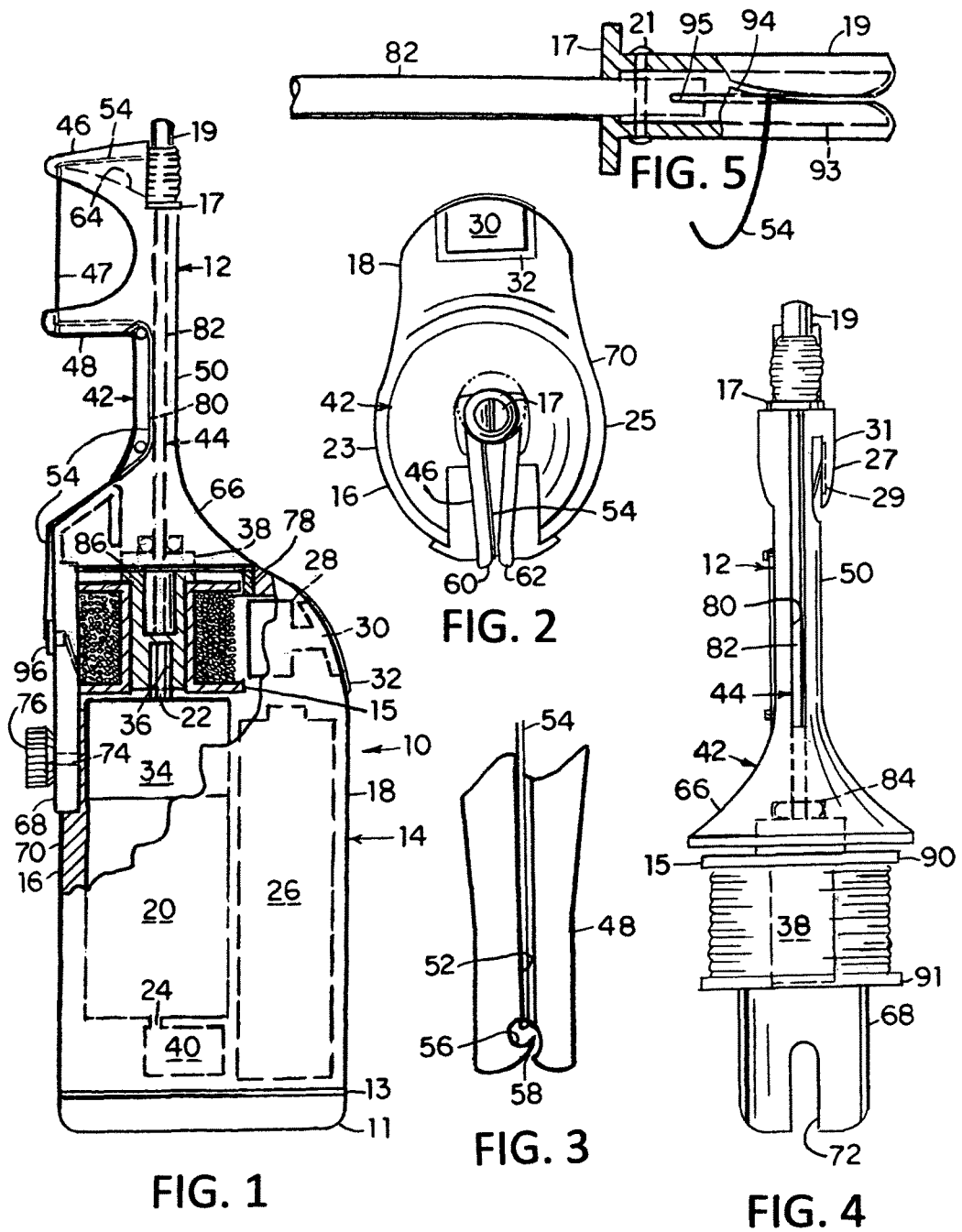

HIGH-SPEED AUTOMATIC DENTAL FLOSSER

CROSS-REFERENCE TO RELATED APPLICATIONS

This application is a continuation-in-part of application Ser. No. 13/849,574.

BACKGROUND

Field

This application relates to dental hygiene devices, specifically to powered dental flossers.

Prior Art

Dental flossing is one of the most important personal hygienic tasks. Flossing contributes to the preservation of teeth, gingival (gum) tissues, jaw bones, and general health. Yet, flossing is avoided by many because conventional methods are tedious, messy, and inefficient. Conventional floss frames supporting a fixed floss span are unhygienic because the floss span becomes septic upon first contact with dentition wherein the device must be frequently replaced. Some products claimed to be "flossers" power-rotate tiny bristles as a substitute for flossing, but this method can't deep-clean interdentally. Proper interdental hygiene requires removal of adherent material from under circumferential gum lines. Other than skilled professional cleaning, only correct flossing strokes using continuously replaced floss spans can suffice.

The patent records show several powered flossers intended to provide continuous automatic floss replacement (CAFR), but none have appeared on the market. A problem in common with CAFR flossers of record reviewed by this inventor is that during use, the used floss (septic floss) is dragged rearward behind the flossing tines to a take-up spool in or on the main body of the flossers. The septic floss contains bacteria and food debris that are difficult to sanitize and results in debris deposits, stains, and offensive odors.

SUMMARY

Embodiments of a more practical dental flosser, shown and described in this application, include a replaceable attachment that winds used floss on a take-up spool positioned over a flossing tine. This restricts used floss to the oral portion of the flosser for rapid disposal of spooled septic floss and expeditious reset of spooled fresh floss. Another attachment features built-in means for sanitizing the used floss and requires no floss-handling by the user. A power driver of the attachments includes a dual-shaft drive system that drives a flossing span to oscillate at high-speed transversely of the span while continuously replacing the span.

Advantages

Some attachment embodiments feature winding used floss at an anterior extremity where septic floss disposal is simple and efficient. The self-sanitizing attachment is maintenance-free. In all embodiments, simultaneous longitudinal and transverse motions of a floss span work the floss between tightly abutting teeth and under circumferential gum lines to remove debris and to polish teeth interdentally.

DRAWINGS

FIGS. 1-9

The accompanying drawings in combination with the description herewith illustrate features of embodiments. Like reference numerals in different views refer to the same parts. The drawings are not necessarily to scale.

FIG. 1 is a lateral side view of an automatic dental flosser including a power driver detachably connected to a detachable flossing attachment, both are shown partly in section taken through a longitudinal midline of the flosser.

FIG. 2 is an enlarged front view of the flosser of FIG. 1.

FIG. 3 is an enlarged fragmental rear view of a second flossing tine of the flosser of FIG. 1.

FIG. 4 is an enlarged top view of the detachable flossing attachment of the flosser of FIG. 1.

FIG. 5 is an enlarged top view, partly in section, of a floss take-up spool of the flosser of FIG. 1.

DETAILED DESCRIPTION

FIGS. 1-6

First Embodiment

Figure 6:
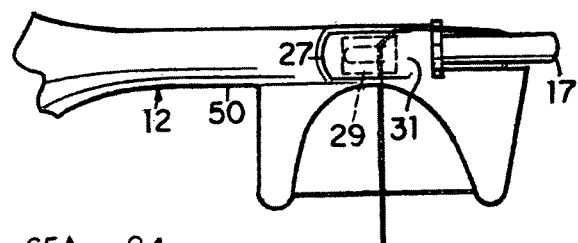
FIG. 6 is an enlarged fragmental side view of an anterior portion of the flossing attachment of the flosser of FIG. 1 showing a floss cutting feature.

Beginning with FIG. 1, an embodiment of the automatic dental flosser 10 is shown including flossing attachment 12 detachably connected to power driver 14 that drives attachment 12. Included in attachment 12 are a flossing arm 50 supporting flossing tines 46 and 48, a floss supply spool 15, floss take-up spool 17, and floss 54 threaded through the attachment.

Components of driver 14 include a hollow plastic housing 70 forming a handle and having a lower semi-cylindrical chamber 16 and an upper semi-cylindrical chamber 18. Tightly fitted in chamber 16 is a dual-shaft geared motor 20 having an anterior drive shaft 22 and a posterior drive shaft 24. Chamber 18 is a holder of an electric power cell 26 for energizing motor 20 by way of a conventional electric circuit (not shown) open or closed by a momentary switch 28. An actuating button 30 of switch 28 is accessible through an opening in chamber 18. Button 30 is covered by a flexible plastic membrane 32 which is sealed water-tight by conventional means. Electrical wires and connectors (not shown) electrically connecting power cell 26, switch 28, and motor 20 are conventional.

A detachable end cap 11 covers an otherwise open posterior end portion of housing 70. Cap 11 can be removed for replacing power cell 26. A conventional rib-and-groove connector (not shown) detachably retains cap 11 in place and a rubber seal 13 around end rims of housing chambers 16 and 18 keeps moisture out.

Geared motor 20 includes a motor-driven speed-reduction gear train (not shown) contained in a gearbox 34. The gear train drives anterior shaft 22 which has a hex-shaped cross section and serves as a key mated and detachably received in a hex-shaped keyway 36 in a flanged cylindrical plastic-molded connector 38. Posterior shaft 24 drives an eccentric weight 40 fixedly mounted on shaft 24 by means of a set screw (not shown) or by being press-fitted. Eccentric weight 40 is positioned posteriorly of more than ¾ of the combined mass of all other components of the flosser including the power cell.

Flossing Attachment—FIGS. 1-6

Flossing attachment 12, shown in FIGS. 1-6, is comprised of two assemblies; an outer assembly 42 (FIG. 1) and an inner assembly 44. Outer assembly 42 is comprised of a bifurcated member forming first flossing tine 46 positioned in front or anteriorly of second flossing tine 48. The tines are spaced from each other and positioned at an anterior or front end portion of arm 50. As shown in FIG. 3, second tine 48 defines a floss guide groove 52 that guides dental floss 54 to a distal end portion thereof. The tine distal end portion defines an aperture 56 through tine 48 wherein aperture 56 is directed toward opposite tine 46. The distal end portion of tine 48 also defines an open-ended slot 58 having its open end at the distal end of tine 48. Slot 58 enters in communication with aperture 56 by entering from a lateral side thereof as viewed when tine 48 is positioned vertically. Slot 58 and aperture 56 together are 9-shaped and serve for expeditiously attaching, guiding, and supporting floss 54 on tine 48 and for avoiding accidental detachment of the floss from tine 48.

FIG. 2 shows that an anterior portion of first tine 46 is formed into two opposing floss shields 60 and 62 positioned proximate to take-up spool 17. Shields 60 and 62 are spaced slightly apart for shielding used floss 54 passing between the shields as the floss is drawn from a distal end portion of first tine 46 to take-up spool 17. Shields 60 and 62 extend anteriorly of tine 46 starting from a location indicated by a dashed line 64 in FIG. 1. The tine shields are substantially triangular-shaped wherein a side of the triangle proximate to spool 17 is parallel to a core 19 of spool 17. The advantage of this arrangement is explained further on in this document. A proximal end portion of arm 50 includes a flange 66 formed to engage power driver 14. Arm 50 with its flange 66 and tines 46 and 48 are formed as a one-piece plastic-molded combination.

Outer assembly 42 also includes a bracket 68 for detachably connecting flossing attachment 12 to power driver 14. Bracket 68 is shaped to conform to plastic housing 70. A hook-shaped front portion of bracket 68 is partially embedded in the molded plastic of flange 66 to fixedly secure arm 50 and bracket 68 together. As shown in FIG. 4, bracket 68 defines a U-shaped slot 72 for receiving a screw 74 (FIG. 1) extending from driver housing 70. A knurled nut 76 holds attachment 12 in place on driver 14 wherein a ring gasket 78 cemented around a rim of driver 14 forms a water-tight seal at the joint. Referring back to FIG. 4, flange 66 defines a multi-diameter central bore aligned with an open channel 80 extending longitudinally of arm 50 and ends at a distal end of the arm.

Inner assembly 44 is comprised of a flexible and resilient driven shaft 82 rotatably supported in the central bore in flange 66. Driven shaft 82 extends longitudinally along channel 80 wherein an O-ring seal 84 seated in a recess in flange 66 and encircling shaft 82 prevents moisture from entering driver 14. A proximal end portion of shaft 82 is fixedly and coaxially imbedded in a sleeve 86 (FIG. 1) which is fixedly and coaxially imbedded in plastic connector 38.

Referring to FIG. 4, rotatably supported on connector 38 is a floss supply spool 15 which includes a pair of floss retaining flanges 90 and 91 fixed to a hollow spool core fitting loosely around connector 38. Spool 15 rotates independently of connector 38 by slipping around the connector.

Shown in FIG. 5, a distal portion of driven shaft 82 is fixedly received in a hollow tube or sleeve 93 which forms a hollow distal end portion of shaft 82. Core 19 of take-up spool 17 is hollow for receiving the hollow distal end portion of shaft 82 fixed therein by a pin 21 passing through a transverse aperture through spool core 19 and through shaft 82. Core 19 defines an open-ended core slit 94 therethrough that curves in a spiral-like manner longitudinally of spool core 19. The hollow distal end portion of driven shaft 82 defines an open-ended linear slit 95 therethrough longitudinally thereof. The open end of spool core slit 94 is aligned with the open end of shaft slit 95. Both slits 94 and 95 progressively diverge away from each other as they extend away from their open ends. They do so to form a floss gripper for enhanced gripping of floss 54 passing from tine 46 and transversely through both slits 94 and 95 to detachably connect floss 54 expeditiously to spool core 19 for being wound thereon.

FIGS. 1-3 show the route for threading floss 54 through flosser 10 starting at supply spool 15 as fresh floss. From spool 15, floss 54 passes through a grommet 96 in bracket 68 and bends around flange 66 to pass over two guide posts projecting from a lateral side of arm 50 for guiding and supporting the floss. A slot at the crotch between arm 50 and tine 48 enables the floss to enter into and pass through the floss guides of second tine 48. From tine 48 the floss forms a flossing span 47 between both tines and then travels between the flossing shields 60 and 62 to take-up spool 17.

As used floss builds up on take-up spool 17, the accumulating spooled floss will engage shields 60 and 62 of the bifurcated member. To accommodate expansion of accumulating spooled floss, flexible and resilient shaft 82 will be forced to temporarily bend slightly for repositioning spool 17. In FIG. 2, the phantom image around spool 17 indicates a raised position of spooled used floss that will occur after a substantial increase of floss accumulation accommodated by the mentioned bending of shaft 82. Hence, the anterior strand of floss 54 between shields 60 and 62, and about to be wound onto spool 17, is adequately shielded during all amounts of floss-winding on the take-up spool.

Referring to FIGS. 4 and 6, a user can dispose of the spooled used floss after flossing one or more times by simply pulling the spooled used floss off the distal end of spool 17. To cut off the used floss, arm 50 includes a conventional floss cutter 29 hidden under a tongue-shaped guard 27 proximate to spool 17. A proximal end portion 31 of guard 27 is molded to a distal end portion of arm 50. Most of guard 27 is spaced from arm 50 to allow floss to slide under the guard to access cutter 29 for cutting off the used floss. The base of cutter 29 is attached to an underside of the guard by being imbedded in the molded plastic. The cutter's cutting blade is angled toward the open entry under the guard to receive and cut floss. Thus, floss can be gripped by the floss gripper in spool core 19 wherein the used portion of floss can then be cut off by cutter 29. Both steps can be done in one or two seconds and the flosser will be ready for use again.

Controlling Tension of the Foss Span—FIGS. 1, 2 and 4

In FIG. 2, driver housing 70 includes opposing anterior lateral side walls 23 and 25. Floss supply spool 15 is between walls 23 and 25 which have interior surfaces that are normally slightly spaced from flanges 90 and 91 of spool 15. Walls 23 and 25 are molded from resilient plastic and sufficiently thin for temporarily bending inward under user hand pressure. Thus, a user can optionally finger-press the exterior of the driver housing such that at least one of the opposing side walls 23 and 25 temporarily bends inward. The walls will engage flanges 90 and/or 91 to produce selective rotation resistance of supply spool 15. This enables user-selective tension of floss span 47. The amount of pressure applied by the user's fingers against the walls determines the amount of floss span tension. Benefits of user-controlled floss-span tension are explained in the Flosser Operation section of this document.

Second Embodiment of a Flossing Attachment

FIG. 7

Figure 7:
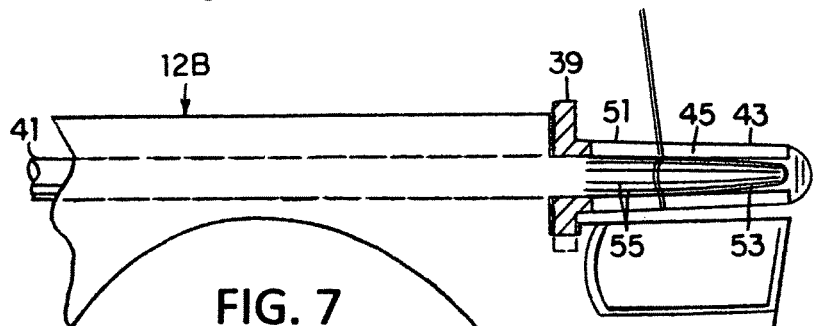
FIG. 7 is an enlarged fragmental side view of an anterior portion of a second embodiment of a flossing attachment showing an alternative floss take-up spool sectioned longitudinally along the spool rotational axis wherein the opposite spool half is removed.

Shown in FIG. 7 is a flossing attachment 12B which is substantially the same as embodiment 12 except for replacement components described next. A plastic floss take-up spool 39, that replaced spool 17, receives a flexible and resilient replacement driven shaft 41 fixed into a hub bore passing longitudinally through an open-ended core 43 of spool 39. Spool core 43 is cone-shaped progressively narrowing toward the open end. (For visability, spool 39 is sectioned longitudinally along the rotational axis wherein a removed opposite half of spool 39 is a mirror image of the one shown.)

Spool core 43 defines an open-ended linear slot 45 in communication with the core hub bore and partially divides core 43 longitudinally into opposed symmetrical core portions including core portion 51. Starting from the open end of core 43, slot 45 progressively narrows as the slot extends rearward away from the open end. The opposed core portions are designed to expeditiously grip floss between them for functions that include detachably connecting the floss to spool 39 for winding the floss. Thus, core 43 forms a floss gripper.

A floss grip enhancer 53 is positioned within the hub bore of core 43 and between the opposing core portions. When floss is drawn into slot 45, grip enhancer 53 serves for detachably jamming or jam-gripping the floss between grip enhancer 53 and the inner surface of core 43. Grip enhancer 53 is an elongate distal end portion of shaft 41 progressively narrowing to a dull point toward the open end of core 43. Conversely, enhancer 53 progressively widens as the shaft extends away from the open end of core 43. In addition, enhancer 53 defines closely juxtaposed longitudinal grooves 55 which result in splines, respectively, between the grooves along the tapered shaft to provide an anti-slip surface thereon for enhanced slip-resistant jam-gripping of floss for winding on spool 39.

Operation of the High-Speed Dental Flosser

The components of flosser 10 are arranged such that a user that operates switch button 30 will have fingers holding the flosser where the user's fingers will act as a seesaw pivot or fulcrum. Hence, oscillation amplitudes generated by rotating eccentric weight 40 will be maximized in the vicinity of the floss span, for high flossing performance, while being minimized in the vicinity of the user's mentioned fingers. Since the flosser can be held at its lateral sides with modest finger pressure, the floss span will oscillate in an elliptical orbit having a vertical major axis. If the flosser is held tighter at its lateral sides, lateral motion will be reduced or resisted wherein the floss span oscillations will move in an approximately linear vertical path. Thus, the user can control the shape of the oscillation path of the floss span.

The flossing attachment is expected to be sold pre-loaded and pre-threaded with floss to be ready for use. The flossing action is so fast that the floss span polishes interdentally as it flosses. To slide floss span 47 between very tight abutting teeth, the user can press lateral sides 23 and 25 of the driver to increase floss span tension (as described above). On the other hand, if the floss span were to get caught on a user's dental appliance, the user can relieve pressure on sides 23 and 25 to slacken and dislodge the floss span. Then pressing button 30 removes the slack and normal operation can proceed.

With regard to maintenance, no floss-handling by the user will be needed for several flossings. After each flossing, the oral portion of the flosser (the portion that contacts the user's mouth) may be rinsed under a faucet and then left in a glass having about an inch of mouthwash for sanitizing the spooled used floss on the take-up spool. Alternatively, the user can skip sanitizing the spooled floss by pulling the used floss off the end of the take-up spool after each flossing. This can be done by first pulling down on floss span 47 wherein fresh floss will be drawn from supply spool 15 to allow slack for pulling off the used floss from spool 17. The fresh portion of floss can then be attached to the take-up spool instantly by use of the floss gripper and the used floss can be cut off on the cutter. The flosser is then ready for the next use. The floss portion attached to the gripper will wind on the take-up spool by pressing switch button 30.

Third Embodiment of a Flossing Attachment

FIG. 8

Figure 8:
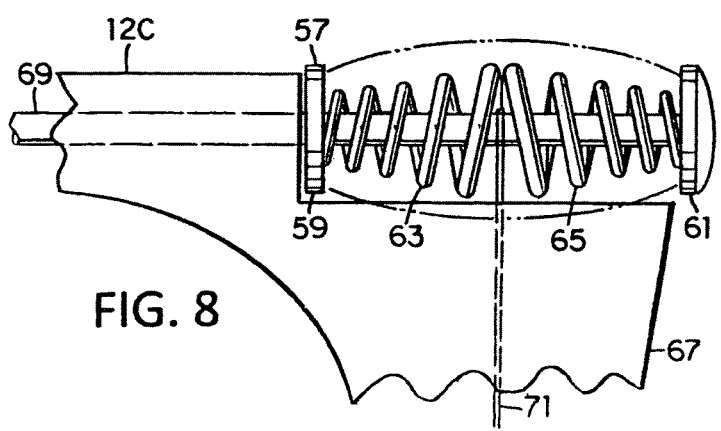
FIG. 8 is an enlarged fragmental side view of an anterior portion of a third embodiment of a flossing attachment showing a floss take-up spool having high floss-holding capacity.

Removal of used floss and reset of fresh floss in the attachments described above is simple and quick. To provide another choice, FIG. 8 shows a flossing attachment 12C that requires no floss-handling at all. Flossing attachment 12C is substantially the same as attachment 12 except for the following changes. The floss cutting feature is left out and a larger floss capacity take-up spool 57 includes floss-retaining disk flanges 59 and 61 at the ends, respectively, of its spool core. The greater floss storing capacity results mainly from the spool having a core with an ability to compel the floss to traverse along the length of the core as the floss is being wound. The core of spool 57 includes a pair of fixedly and coaxially connected augers 63 and 65. Each being generally tapered or conical in shape and joined at its base or largest diameter with that of the other auger. Auger 63 has a right hand helical thread or flight and auger 65 has a left hand helical thread or flight so that the spool can be rotated such that each auger will push winding floss in a direction away from the other auger.

Augers 63 and 65 are plastic molded integrally with flanges 59 and 61 and a flexible and resilient driven shaft 69 as a one-piece unit. A first flossing tine 67 of attachment 12C guides an incoming used floss strand 71 initially toward the middle of the core of spool 57 and approximately perpendicular to the core. When spool 57 is rotated in the mentioned direction, floss being wound on the spool core will be compelled to first traverse one auger toward its distal end. The slope of the accumulating floss coil and the natural tendency of the strand to return to the perpendicular position will urge the strand back to the middle of the core wherein the opposite auger takes over and the process is repeated thereon.

Eventually, both augers become covered with spooled floss and the floss will be broadly distributed on the spool core. The phantom lines around the core of spool 57 indicate a potential distribution of floss wound on the spool.

Except for the floss, flossing attachment 12C can be molded entirely of plastic at low cost. After take-up spool 57 is filled with floss, attachment 12C can then be discarded and replaced with another one pre-loaded and pre-threaded with floss. Each attachment can be used several times without any floss-handling by the user.

A version for single-use by dental hygienists may be devised having very small supply and take-up spools. Single-use attachments may be discarded and replaced after use on each patient. The benefit is the ability to simultaneously floss and polish surfaces between teeth at high speed, thereby saving time.

Forth Embodiment of a Flossing Attachment

FIG. 9

Figure 9:
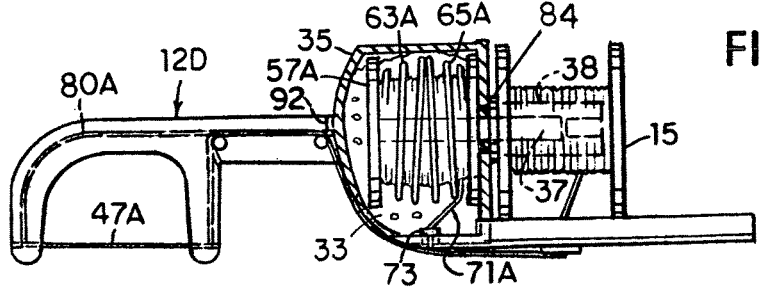
FIG. 9 is an enlarged side view, partly in section, of a fourth embodiment of a flossing attachment requiring no floss maintenance by the user.

Shown in FIG. 9 is flossing attachment 12D which incorporates features of attachment 12C of FIG. 8, but is intended for a large number of uses before being discarded. This maintenance-free embodiment requires no floss-handling by the user and can store a substantial amount of used floss hygienically before disposal. A take-up spool 57A is structurally similar to spool 57 but is larger, especially in diameter. Spool 57A has a core comprising a pair of fixedly and coaxially connected cone-shaped augers 63A and 65A. Auger 63A has a right hand helical thread or flight and auger 65A has a left hand helical thread or flight so that the spool can be rotated such that each auger will push winding floss in a direction away from the other auger. The augers 63A and 65A are arranged like augers 63 and 65 and are plastic molded integrally with the spool end flanges and with a driven shaft 37 as a one-piece unit.

Take-up spool 57A is completely enclosed on all sides by a fluid-tight (liquid and gas tight) plastic capsule 35 integrally molded together with a bifurcated member. In production models, the capsule can be molded as two separate halves cemented together after enclosing the spool. Also enclosed in capsule 35 is a broad-spectrum high-viscosity antiseptic liquid 33 which is injected into the capsule through an aperture for fluid-tightly receiving a rubber plug made into a floss bearing 73 before the bearing is installed. Spool 57A is submerged in the antiseptic liquid while being attached to a floss strand 71A that passes into the capsule through bearing 73. Strand 71A is inserted through the center of bearing 73 by means of a sewing needle at the manufacturing plant before assembly of the attachment. During the insertion, the needle compresses the rubber around the needle until the needle and floss pass through bearing 73. Then the rubber resiliently springs back to form a fluid-tight compression-seal around the floss resulting in the bearing being fluid-tight. This prevents antiseptic liquid and chemical odors from leaking out of the capsule. During winding, used floss is drawn through the floss bearing and is sanitized by the antiseptic liquid to prevent bacterial activity.

A posterior wall of capsule 35 defines an aperture surrounded by an O-ring seat for fluid-tightly supporting O-ring 84 encircling driven shaft 37. A posterior portion of shaft 37 is fixedly and coaxially embedded in connecter 38 for being driven to rotate spool 57A by driver 14. As in the other attachments, floss supply spool 15 rotates independently of connecter 38 by slipping around the connecter as floss is drawn off spool 15.

Floss from supply spool 15 is guided by floss guides similar to those described for attachment 12 and passes to the bifurcated member to form floss span 47A. From there, the floss travels to capsule 35 via a channel 80A which is similar to channel 80. A proximal end portion of the bifurcated member defines a slot 92 where used floss exits from channel 80A through a lateral side of the bifurcated member opposite the lateral side that guides fresh floss. From there the floss travels through bearing 73 where it enters capsule 35 and connects to spool 57A as strand 71A.

When flossing attachment 12D is attached to driver 14 and driven to wind used floss and to oscillate the floss span during flossing, augers 63A and 65A compel the incoming used floss to traverse and distribute broadly on the core. In addition, the augers serve as impellers that circulate antiseptic liquid 33 to enhance the sanitizing effects.

FIG. 9 shows that most of the floss from spool 15 has been wound onto take-up spool 57A. When the supply floss on spool 15 runs out, attachment 12D can be discarded and replaced with a new one preloaded and pre-threaded with fresh floss. From the above description, it can be understood that attachment 12D requires no maintenance other than rinsing the oral portion under a faucet after each use.

SCOPE AND CONCLUSION

While the description above is of specific embodiments along with some of their uses and applications, these should not be construed as limitations on their scope, but rather as practical examples. The embodiments shown can result in more than one choice of models especially because a model for personal use may differ from a model for professional use.

Other embodiments are also possible. The floss-cutting feature, for example, may alternatively be mounted flanking an upper portion of one of floss shields 60 or 62. In that position, the floss-cutting feature would still be conveniently proximate to the take-up spool for cutting off used floss. On the other hand, a flossing attachment made for professional use will not require a floss cutter because the attachment will be discarded after being used on one patient. The power driver for use by a dental professionals, however, will be used for many patients and may therefore have a stainless steel housing or be adapted to an air-driven dental handpiece. Dental tapes may substitute for floss and either one may carry one or more compounds that provide special scents, flavors, whitening, sanitizing, or polishing ability.

The power and amplitude of the oscillations generated by power drive 14 can be adjustable by the addition of a variable resister to the electric circuit. Alternatively, such amplitude adjustments can be achieved by making the eccentric weight changeable to eccentric weights of different mass. This can be done by threading a distal end portion of the posterior shaft to mate with a threaded aperture in each of a selection of different eccentric weights provided to buyers of the product. The thread should be spiraled to tighten in the opposite direction of the shaft rotation. Removal of detachable cap 11 provides user-access for making weight changes to suit individual users.

Color-coding or number-coding the flossing attachments can be a convenience for personalizing them in a household having more than one user of the automatic flosser. Thus, the driver can be shared without sharing flossing attachments.

An advantageous brushing attachment may be an added feature enabled by the rotational and high-speed oscillatory movements produced by the driver. Such a brushing attachment would have the advantages of being rotated and oscillated simultaneously.

Thus, the scope of the embodiments should be determined by the appended claims and their legal equivalents rather than by the examples given.

What is claimed is:

1. A dental flosser attachment detachably connectable to a power driver, the attachment comprising:
   a bifurcated member forming a pair of flossing tines for movably supporting a dental floss span between said tines for flossing teeth;
   a rotatably supported floss supply spool connected to said bifurcated member for replacing used floss spans with fresh floss spans;
   a rotatably supported floss take-up spool connected to said bifurcated member for being driven by said driver to wind used floss drawn from said tines; and
   a fluid-tight capsule enclosing said take-up spool for preventing escape of odorous gas from inside of said capsule while allowing entry and winding of used floss therein, wherein said take-up spool is at least partially submerged in an antiseptic fluid for inhibiting bacterial activity in said capsule.

2. The dental flosser attachment as defined in claim 1 wherein said capsule includes a wall supporting an elastic floss bearing forming a fluid-tight self-adjusting compression seal around dental floss entering said capsule.

3. The dental flosser attachment as defined in claim 1 further comprising said take-up spool including a core having an auger for distributing plural layers of floss along said core while being wound thereon.

4. The dental flosser attachment as defined in claim 3 wherein said auger includes a right hand helical flight and said attachment further comprising a second auger having a left hand helical flight coaxially joined and helically continuous with said right hand helical flight such that both augers serve for distributing plural layers of floss along said core while being wound thereon.

5. The dental flosser attachment as defined in claim 4 wherein each of the augers is at least partially tapered longitudinally and attached to the other auger at the largest diameter thereof.

6. A dental flosser attachment detachably connectable to a power driver, the attachment comprising:
   a bifurcated member forming a pair of flossing tines for supporting a floss span between said tines for flossing teeth, said bifurcated member being connectable to said driver;
   a rotatably supported floss take-up spool connected to said bifurcated member for being driven by said driver to wind floss coming from said tines, said take-up spool having a core forming an auger for distributing plural layers of floss along said core while being wound thereon, said auger includes a right hand helical flight and said attachment further comprising a second auger having a left hand helical flight coaxially joined and helically continuous with said right hand helical flight such that both augers serve for distributing plural layers of floss along said core while being wound thereon; and
   a floss guide positioned adjacent said core for leading the floss to said core.

7. The flosser attachment as defined in claim 6 wherein said floss guide being positioned approximately equidistant from each auger to lead floss initially toward the middle of the core length for enabling the floss to traverse both augers.

8. The flosser attachment as defined in claim 6 wherein each auger being at least partially tapered and forms a base portion having the largest diameter of the auger.

9. The flosser attachment as defined in claim 8 wherein the augers being joined together at their base portions.

10. The flosser attachment as defined in claim 6 further comprising a fluid-tight capsule enclosing said take-up spool for preventing escape of odorous gas from inside of said capsule while allowing entry and winding of used floss therein.

11. The dental flosser attachment as defined in claim 10 wherein said capsule includes a wall supporting an elastic floss bearing forming a fluid-tight self-adjusting compression seal around dental floss entering said capsule.

* * * * *